US009962747B2

(12) United States Patent
East

(10) Patent No.: US 9,962,747 B2
(45) Date of Patent: May 8, 2018

(54) BIOMOLECULAR ZONAL COMPOSITIONS AND METHODS

(71) Applicants: Bryan Sims, St. Charles, IL (US); Ray East, Beaconsfield, Buckinghamshire (GB)

(72) Inventor: Ray East, Beaconsfield (GB)

(73) Assignees: Bryan Sims, Geneva, IL (US); Ray East, Beaconsfield (GB)

( * ) Notice: Subject to any disclaimer, the term of this patent is extended or adjusted under 35 U.S.C. 154(b) by 0 days. days.

(21) Appl. No.: 15/053,928

(22) Filed: Feb. 25, 2016

(65) Prior Publication Data

US 2016/0250673 A1    Sep. 1, 2016

Related U.S. Application Data

(60) Provisional application No. 62/121,127, filed on Feb. 26, 2015.

(51) Int. Cl.
| | |
|---|---|
| *B09C 1/00* | (2006.01) |
| *B09C 1/10* | (2006.01) |
| *C12N 1/20* | (2006.01) |
| *C02F 3/34* | (2006.01) |
| *C02F 103/06* | (2006.01) |

(52) U.S. Cl.
CPC ............ *B09C 1/10* (2013.01); *B09C 1/002* (2013.01); *C12N 1/20* (2013.01); *B09C 2101/00* (2013.01); *C02F 3/348* (2013.01); *C02F 2103/06* (2013.01); *Y02W 10/45* (2015.05)

(58) Field of Classification Search
CPC .. A61K 2300/00; A61K 38/363; A61K 38/38; A61K 38/39; A61K 38/4833; A61K 45/06; A61K 31/728; A61K 31/79; A61K 38/40; A61K 31/00; A61K 31/02; A61K 31/122; A61K 31/13; A61K 31/4164; A61K 31/732; A61K 31/734; A61K 31/78; A61K 36/886; A61K 38/42; A61K 41/0042; A61K 47/02; A61K 47/34; A61K 47/60; A61K 47/62; A61K 49/0404; A61K 9/0024; A61K 38/47; A61K 47/32; A61K 47/36; A61K 47/6921; A61K 51/1251; A61K 8/66; A61K 9/0019; A61K 9/006; A61K 9/7007; A61B 17/11; A61B 17/12022; A61B 17/12186; A61B 17/1219; A61B 17/12099; A61B 17/12109; A61B 17/1214; A61B 17/12168; A61B 17/06; A61B 17/68; A61B 17/00491; A61B 17/12045; A61B 17/12136; A61B 17/1215; A61B 17/12172; A61B 17/12177; A61B 2017/00004; A61L 31/16; A61L 2300/412; A61L 27/54; A61L 2300/00; A61L 2430/38; A61L 2430/20; A61L 24/043; A61L 27/20; A61L 27/50; A61L 2300/432; B09C 1/002; B09C 1/10; B09C 2101/00; B33Y 80/00; C02F 2103/06; C02F 3/348; C12N 1/20; C12N 9/2405; Y02W 10/45; A61F 2250/0067; A61F 2/86; A61F 2230/0006; A61F 2230/005; A61F 2/01; A61F 2/013; A61M 2025/09175; A61M 25/09; A61N 1/3625; A61N 1/36521; A01N 25/34; A01N 63/02; A01N 63/00; A61Q 11/00; C12Y 302/01028; Y10T 29/49826
See application file for complete search history.

(56) References Cited

U.S. PATENT DOCUMENTS

2002/0098982 A1    7/2002  Burnham

OTHER PUBLICATIONS

International Search Report from International Patent Application No. PCT/US2016/019706, dated May 16, 2016.
Demitri et al., "Potential of Cellulose-Based Superabsorbent Hydrogels as Water Reservoir in Agriculture," International Journal of Polymer Science (2013), pp. 1-6.
Zohuriaan-Mehr et al., "Superabsorbent Polymer Materials: A Review," Iranian Polymer Journal (2008), 17(6), pp. 451-477.

*Primary Examiner* — Deborah K Ware
(74) *Attorney, Agent, or Firm* — Greer, Burns & Crain, Ltd.

(57) ABSTRACT

A composition is provided including biospheres and bacteria, wherein the biospheres are cellulosic biopolymers and sized in the range from 500 nanometers to 80 microns and have a minimum free swell absorption capacity of 400 times by weight and a maximum free swell absorption capacity of 1200 times by weight, wherein the composition is formable as a gelatinous matrix.

11 Claims, 3 Drawing Sheets

BIOMOLECULAR ZONAL COMPOSITIONS AND METHODS

RELATED APPLICATION

This application claims priority under 35 USC 119 from U.S. Provisional Application Ser. No. 62/121,127 filed Feb. 26, 2015.

FIELD OF THE INVENTION

This invention relates to compositions and methods for bioremediation of land. The compositions comprise biospheres and allow for bioremediation in-situ.

BACKGROUND

Bioremediation has emerged as a promising technology for the treatment of soil and groundwater contamination. Some conventional bioremediation approaches require the soil to be excavated for treatment either off site or ex-situ. Disadvantages of these approaches include disruption of the natural field and the need to transport large quantities of contaminated soil.

It would be beneficial to establish a bioremediation system in-situ in the field and without the need for transporting the contaminated soil or water. Methods for bioremediation in the field can use certain bacteria which digest and neutralize contaminants. Often, these bacteria are provided as a liquid culture. In these methods, water is used as a carrier to deliver bacteria and/or nutrients to the treatment area in the field. However, utilizing water as a medium to deliver and distribute bacteria is associated with various problems. Bacteria require moisture. However, simple liquid or water cultures in-situ cannot maintain sufficiently the moisture level because water tends to evaporate and this causes massive losses in potential microbial activity. Hence, establishing and sustaining sufficiently large microbial populations at the contamination site becomes problematic.

Bacteria obtain from their environment all nutrient materials necessary for their metabolic processes and cell reproduction. The food must be in solution and must pass into the cell. This is especially difficult when treating contamination in-situ due to high levels of toxicity being present at the start of a treatment and the lack of food that is inevitable towards the end of the process. Further, aerobes need oxygen for respiration and cannot grow unless oxygen is provided. Additionally, bacteria have a pH range within which growth is possible. Although the optimum pH value differs between species, an environment that is maintained to a neutral pH will best sustain most bacterial species utilized for in-situ bioremediation.

Successful bioremediation requires optimizing biomass in-situ, as this represents the total amount of suitable bacteria present in a given area or volume that will have the potential to metabolize and break down the contamination in order to remediate the targeted area of pollution.

The fate of in-situ bioremediation is generally considered to be uncertain when utilizing water as a medium to distribute bacteria because water is fluid and it is difficult to localize the distribution and delivery to one area. The process may become wasteful and massive amounts of bacterial inoculate may be lost through natural migration. Moreover, much of the bacteria often misses the targeted pollution entirely, as the liquid culture passes through the soil too quickly to allow the formation of molecular bonds that are essential to both establishing and sustaining an effective process of biodegradation.

Thus, there remains the need in the field for compositions and methods of delivering bacteria and other microorganisms in-situ for bioremediation of land and water.

SUMMARY

At least some of these needs are addressed by remediation compositions and methods provided in this disclosure and suitable for treatments in-situ. One embodiment provides compositions and methods for natural biodegradation of organic waste. Further embodiments provide compositions and methods for decontamination of soil, hard surfaces and construction materials such as bricks, concrete, gravel and stone masonry in the field.

Other embodiments provide compositions and methods for decontamination of water in the field, such as for example, ocean water, ground water and rivers.

One of the advantages of these compositions and methods is the reduction in number of in situ applications needed in comparison to conventional compositions and methods.

Suitable bacteria include, but are not limited to, naturally occurring bacteria and genetically engineered bacteria. Some suitable bacteria include those that produce at least one enzyme that can be used for biodegradation of organic waste. A person of skill will further appreciate that in addition to bacteria, other microorganisms, such as for example algae, can be suitable in certain embodiments.

One embodiment provides a composition that transforms water from being a simple carrier into a host environment where microbial activity can thrive. The composition creates an organic gelatinous matrix and is well suited for delivering, sustaining and containing microorganisms in situ at a contamination site. The network is easy to manage and localize to a contamination zone in part because it has a very slow migratory rate and will remain in place at the contamination site long enough for bacteria to digest and clean the organic waste.

One embodiment provides a blend which transforms liquid microbial culture into continuous gelatinous superstructures that can act as the bacteria's essential foundation for life as they store key elements such as carbon, hydrogen, oxygen and nitrogen.

In some embodiments, the blend is mixed with absorbent cellulosic biopolymers that range in size from between 500 nanometers to 80 microns. In addition to forming a cellular, rather than crystalline matrix when hydrated, these tiny particles, which are referred to in this specification as biospheres, must have a minimum free swell absorption capacity of 400 times by weight and a maximum of 1200 times.

This range is critical in terms of achieving the correct carbon balance for each gelatinous mixture. This delicate balance is caused by the necessity to provide sufficient levels of carbon as a food source to sustain optimized levels of microbial activity, but not overloading the mixture with carbon to the point where it becomes possible for the genome, in the bacteria, to adapt towards favoring food that is easier to digest and, as a consequence, encouraging the microbial process to switch off from the food source being targeted, which is the contamination.

In some embodiments, the blend carries biospheres that act like tiny building blocks in the ground to supplement the soil's retentive processes and its ability to redistribute various essential elements. This optimizes the life support system that represents the host environment within the land or contaminated water source, and, thus, the blend can significantly increase a specific biomass and the potential for biodegradation wherever it is needed within the profile of the soil or contaminated water source.

The biospheres that form the basic molecular structure within the blend have the ability to release moisture. Primarily, this action facilitates a process of slow release for a range of critical life supporting constituents which are rapidly lost when applying conventional liquid cultures, and, significantly, the biospheres, that remain, can be recharged by either simple human intervention or, in a number of scenarios, remotely through nothing more than rehydration by capturing the rain.

It should be noted that conventional synthetic super absorbent polymers are much less suitable for the production of these biological blends. They would form molecular structures that would be inimical, rather than optimizing to the microbial process.

Further embodiments provide a method which creates an adaptable living gelatinous matrix by transforming water into a sustainable host microenvironment which optimizes the process of biodegradation and represents a major difference and advance over conventional bioremediation using liquid cultures.

In further embodiments, the blend with biospheres can be used with water and a broad range of biological and chemical reagents with scope for application on any scale. The blend assists organic molecules to dissolve, mix and interact with bacteria to optimize the process of predictable in-situ bioremediation, notwithstanding that the number of treatments are minimized—even in scenarios where no potential for biological activity exists.

The blends with biospheres can be devised and engineered so that they suit specific applications. Hence, selecting the most appropriate particle size, when producing site specific blends with biospheres, represents an important part of this technology. Typically, the size of particles utilized in the blends fall into five main categories, as discussed in more detail below.

Some embodiments provide blends and methods for treating the soil surface in-situ. In these applications, the dynamic viscosity is level 1 and biospheres are greater in size than 500 nanometers to avoid excessive reactivity that, due to their very large surface area to volume ratio, can cause agglomeration in the soil, but, equally important, is that they are less than 5 microns to ensure the particles are not filtered out as the blend migrates through the soil. The viscosities of these blends are between Factors 3 and 6, dependent upon geology and contamination, wherein factor 3 equals 6 centipoise (cps) and factor 6 equals 217 cps.

Some other embodiments provide blends and methods for treatment of soil surfaces where gelatinous matrix should have a higher viscosity which is valued as dynamic viscosity levels 1 and 2. In these blends and methods, biospheres are in the range between 10 and 30 microns to avoid deep penetration into the soil. The viscosity ranges of these blends are between Factor 6 & 14, dependent upon geology and contamination, wherein Factor 6 equals to 217 cps and Factor 14 equals to 1,159 cps.

Further blends and methods include those suitable for in-situ treatment of porous hard surfaces. In these blends, the dynamic viscosity levels are 1 and 2 and biospheres are in the range between 5 & 40 microns to achieve sufficient penetration and provide an adequate coating across the surface being treated to sustain an optimized level of microbial activity. The viscosity ranges of these biospheres are equal to Factors of between 6 and 18, dependent upon surface material and contamination and wherein Factor 6 is equal to 217 cps and Factor 18 is equal to 1,236 cps.

Further blends and methods are suitable for treatment of non-porous hard surfaces with dynamic viscosity Levels 2 and 3. In these blends, biospheres are in the range between 30 and 80 microns to provide an adequate coating across the surface being treated to sustain an optimized level of microbial activity. The viscosity ranges of these biospheres are equal to a Factor between 18 and 36, dependent upon surface material and contamination, wherein Factor 18 equals to 1,236 cps and Factor 36 equals to 5,021 cps. Dynamic Viscosity Level 3 is particularly suitable for treating heavy contamination where surfaces require high levels of moisture retention due to little or no on-site attendance.

Further embodiments provide blends and methods for in situ treatment of vertical surfaces with dynamic viscosity levels between 3 and 4. In these blends, biospheres are in the range between 40 and 80 microns to provide an adequate coating and attachment across the surface being treated to sustain an optimized level of microbial activity. The viscosity ranges of these biospheres are equal to a Factor of between 36 and 72, dependent upon surface material and contamination, wherein Factor 36 equals to 5,021 cps and Factor 72 equals to 47,311 cps.

In some embodiments, the blends are applied to provide an optimizing microbial wrap or coating that interacts, in-situ, with surfaces that are saturated by a pretreatment utilizing either a symbiotic low viscosity with Factor 3 or liquid culture.

These treatment categories demonstrate one of the advances presented by this technology over using simple liquid cultures: the ability of the blend with biospheres to adapt biological hosts for the optimized distribution of selected bacteria in a form devised to suit specific treatment requirements based upon the type of geology and surfaces to be remediated, and also accounting for the weather and accessibility to the location requiring treatment. Even in highly problematic cases, where it would be impossible to treat using conventional liquid cultures, the blends with biospheres can be adapted to provide an optimized biological solution e.g. when pollution is located on vertical surfaces, such as brick walls, which can be affected by contamination, through subsurface migration, in an underground tunnel.

More specifically, a composition is provided including biospheres and bacteria, wherein the biospheres are cellulosic biopolymers and sized in the range from 500 nanometers to 80 microns and have a minimum free swell absorption capacity of 400 times by weight and a maximum free swell absorption capacity of 1200 times by weight, wherein the composition is formable as a gelatinous matrix.

In another embodiment, a method is provided for bioremediation in situ, including:

preparing a blend of liquid bacterial culture with biospheres, wherein the biospheres are cellulosic biopolymers and sized in the range from 500 nanometers to 80 microns and have a minimum free swell absorption capacity of 400 times by weight and a maximum free swell absorption capacity of 1200 times by weight;

applying the blend at a site in need of bioremediation; and forming a gelatinous matrix with the blend.

In still another embodiment, a method is provided for delivering and/or hosting biological and/or chemical reagents in a gelatinous matrix, the method including:

obtaining biospheres which are cellulosic biopolymers and sized in the range from 500 nanometers to 80 microns and have a minimum free swell absorption capacity of 400 times by weight and a maximum free swell absorption capacity of 1200 times by weight;

mixing the biospheres with a bacterial and/or chemical reagent to form a mixture; and forming a gelatinous matrix with the mixture.

DETAILED DESCRIPTION

Figure 1:
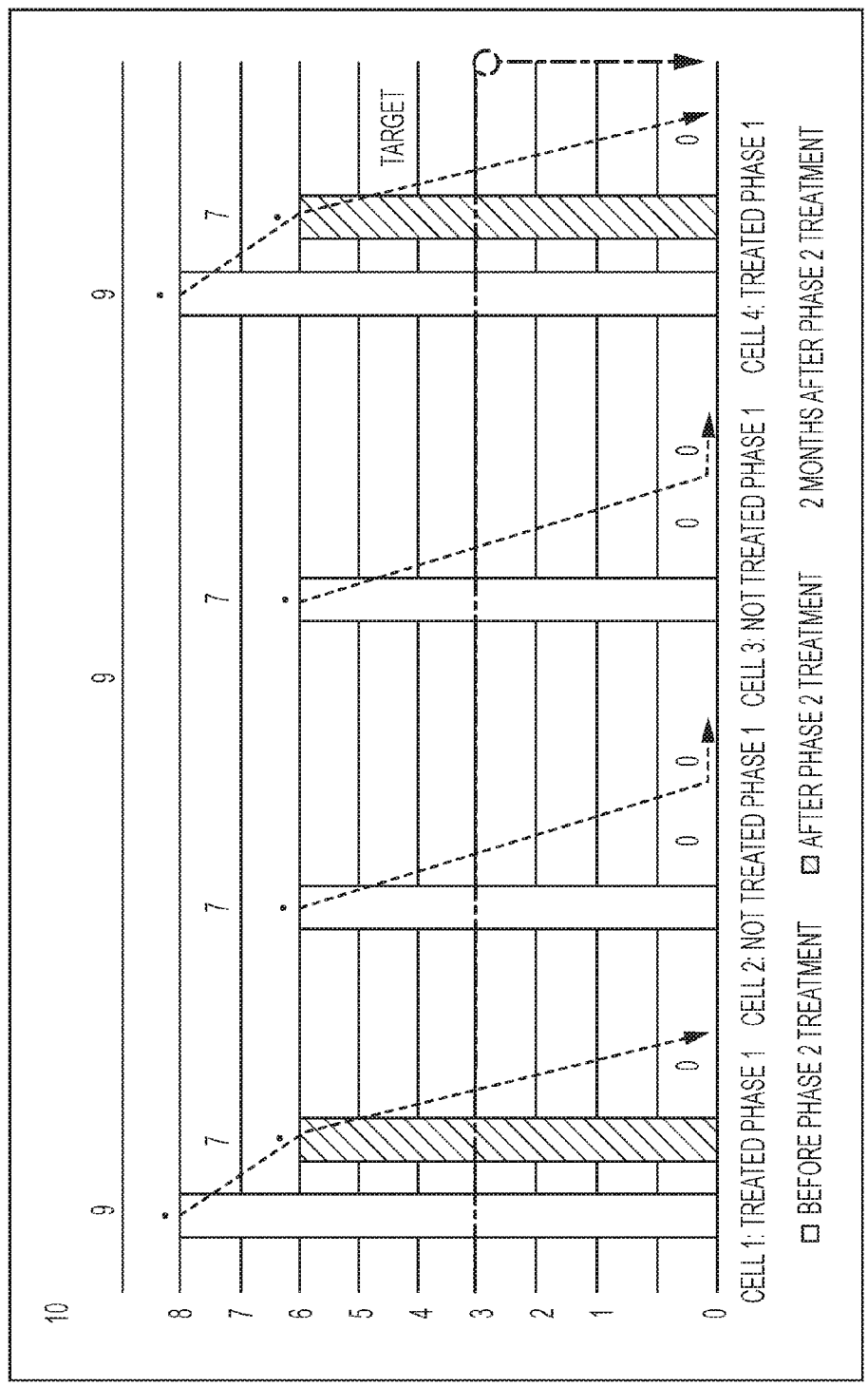
FIG. 1 reports results from treatment with average hot spot concentrations (>5,000 mg/kg)
Figure 2:
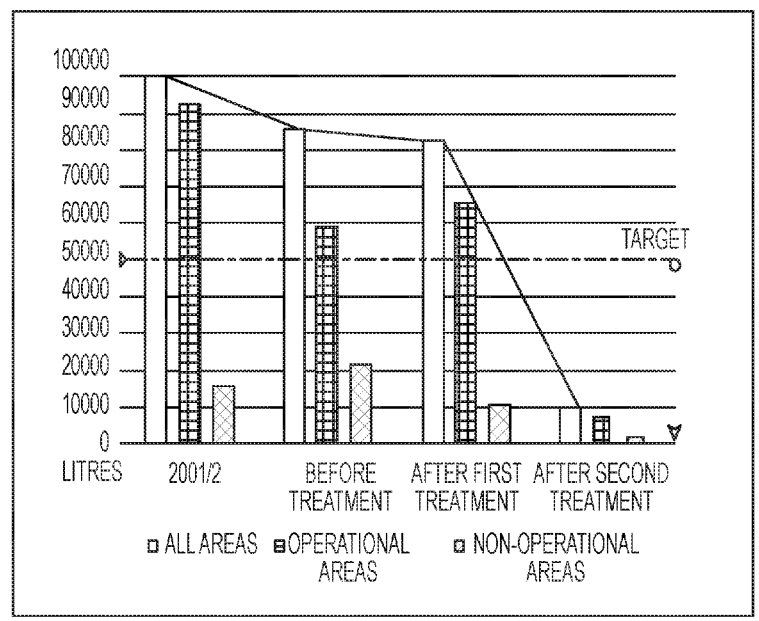
FIG. 2 reports volumetric projections.

In all these novel applications and treatment applications, both field and bench-scale studies, have demonstrated the ability of the blends with biospheres to enhance the process of biodegradation. As a result, many of the active properties that combine to produce these highly productive outcomes also distinguish the in-situ technology with biospheres from conventional bioremediation.

One particularly important distinction is the capacity to establish and sustain microbial activity at levels where potent micellar bio-surfactant solutions naturally occur and assist organic molecules to dissolve, mix and interact with the selected bacteria to simplify application and optimize the process of biodegradation.

These optimized, naturally occurring, environmentally safe biological catalysts disrupt the complex molecular chains of hydrocarbon based contaminants and, this process within the gelatinous matrix created by the blend with biospheres, produces more easily digestible molecules that become encapsulated, together with the bacteria, in cores of nano-sized micelles that sustain favorable contact with the water that surrounds them and, thus, provide an ideal microenvironment for optimizing the reaction kinetics associated with successful in-situ biodegradation.

Therefore, the blend with biospheres provides an optimized bioremediation process in which nano-sized micelles are created, while typically no micelles are usually created in a typical bioremediation process with liquid bacterial culture. This distinction is important because of the following significant advantages, which become apparent, when comparing the key characteristics of using the blend with biospheres rather than a conventional liquid culture to perform in-situ biological treatments.

Water's natural ability to freely migrate through the soil and flow across its surface, is as essential for life as it is wasteful and impractical when being used as the primary vehicle for distribution of specific treatments to enrich or remediate the soil. Therefore, with no alternative to water, other than the way it comes out of a tap, for the distribution of specialist biodegrading bacteria, in-situ bioremediation remains a highly unpredictable and intensive procedure. In complete contrast, the blend with biospheres augments water, and while it remains fluid and continuous, it also becomes a controllable life optimizing gelatinous host, which is organic with a cellular matrix to optimize the potential for biological life cycles to thrive.

Despite being a much less intensive process, the gelatinous matrix, which is rechargeable in-situ, is also a far more predictable inoculant than conventional liquid cultures. The blend with biospheres combines absorption, rapid capture and controlled release, within a microbial inoculant, transforms the water element into an optimizing super carrier that can act as a biodegradable subterranean sink, to sustain moisture levels. The gelatinous matrix makes maintaining sufficient moisture and, consequently, in-situ remediation, much more efficient.

Further and also in complete contrast to conventional liquid cultures, the blend with biospheres establishes a natural nutritious reservoir in the ground or across any surface when it is applied. This presents a major advance as the novel properties, within this gelatinous reservoir, of rechargeable super absorption, rapid capture and slow release combine to help even out the unpredictability associated with microbial survival. The most critical stages being at the start of a project, due to contamination causing high levels of toxicity, and towards the end of the process, when a lack of food occurs as a result of the land becoming clean again.

Another significant advance, is controlled migration through dynamic viscosity management so a gelatinous matrix with biospheres and bacteria can radiate through the soil more slowly. This is important as additional control maximizes the opportunity for bacteria to attach themselves to the target food source, which is the contaminant to be removed from the soil or water source. This major difference creates the possibility for establishing billions more Colony Forming Units (CFUs) far more quickly, thus, making the whole procedure faster and much more predictable.

Another advantage, from what occurs within the gelatinous matrix with biospheres, is helping air to flow through the soil by creating micro-pressures as it expands and contracts in the ground. This positive influence over the process is a direct consequence of the cyclical process of capturing and releasing water and nutrients that sustain high levels of microbial activity to, ultimately, optimize the process of in-situ bioremediation.

In at least some embodiments, blends with biospheres are formulated to act as a self-buffering system to independently maintain the correct pH value in the soil throughout the entire treatment process. Moreover, the exceptionally high retention characteristic within blends with biospheres results in a far greater proportion of its pH buffering components remaining in position for much longer than would be possible when using a conventional liquid inoculant and, thus, the blend with biospheres optimizes the potential for these components to act as a continuous bacteria specific pH buffering stimulant.

To prevail over the many limitations facing conventional in-situ bioremediation, the blend with biospheres transforms water to intensify targeting and interaction with contaminants, while still sustaining a healthy microenvironment that optimizes the potential for biological life cycles to flourish. This transformation massively increases the surface area that is made available for the bacteria to grow up on and, thus, the biomass that results is also increased exponentially.

These advances are realized as organic micro-particles (biospheres) are meticulously blended with a water based liquid culture and optionally with other natural synergistic ingredients to develop both site and application specific embodiments.

In some embodiments, the blend with biospheres can be further formulated with at least one component selected from Table 1.

TABLE 1

Components for Heterotrophic Bacterium Growth.

| Component | Minimum Amount (per liter) | Function of Component |
|---|---|---|
| Sodium Citrate ($Na_3C_6H_5O_7$) | 10 g/1.0% | C & Energy Source |
| Ammonium Sulfate ($(NH_4)_2SO_4$) | 1 g/0.1% | pH buffer; N & P Source |
| Monosodium phosphate ($NaH_2PO_4$) | 2.5 g/0.25% | pH buffer; P & K Source |
| Dipotassium Phosphate ($K_2HPO_4$) | 2.5 g/0.25% | pH buffer; P & K Source |
| Magnesium Sulfate ($MgSO_4$); or Eprom Salt ($MgSO_4 \times 7H_2O$) | 0.207 g/ 0.0207% | S & $Mg^{++}$ Source |
| Ferrous Sulfate ($FeSO_4$) | 0.01 g/0.001% | $Fe^{++}$ Source |

In some embodiments, the blend with biospheres and other optional components discussed above, is obtained by using a vacuum induction system so that the biospheres are mixed with the water under intense sheer energy. This is essential as it increases the specific surface of the available liquid by several hundred thousand times and, thus, as the biospheres are separated momentarily, they become wetted and dispersed completely without forming any lumps through agglomeration.

Finally, the blend can be further refined by low to medium rotation before being left to rest and bottling.

Figure 3:
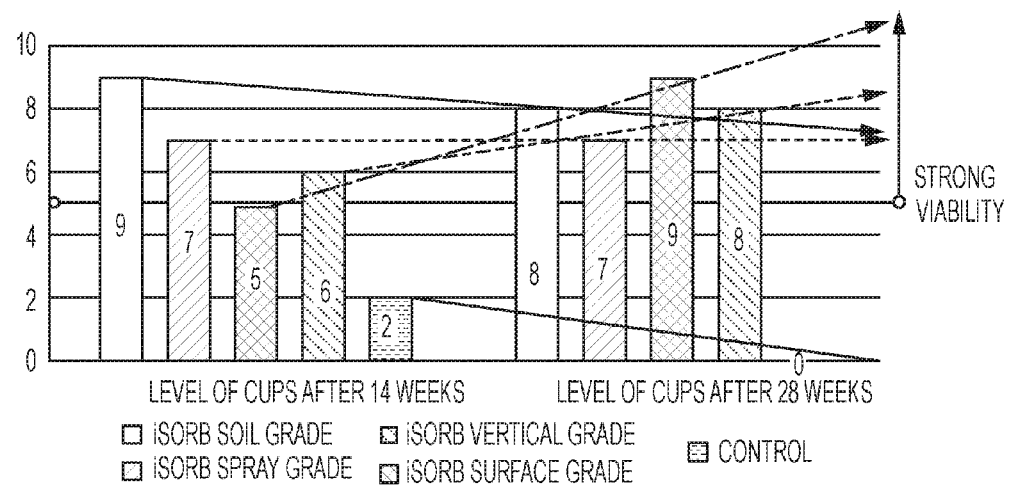
FIG. 3 reports results of a CUP analysis after 14 and 28 weeks.

Rechargeable in-situ, the resulting cellular microenvironment provides a surface area that has the capacity to establish and sustain microbial activity at levels where potent micellar surfactant solutions naturally occur and assist organic molecules to dissolve, mix and interact with the selected bacteria to simplify application and optimize the process of biodegradation.

The blend with biospheres can be used with any microorganisms. At least in some embodiments, the microorganisms utilized are indigenous to the soil and the ocean, they are not genetically altered and fall within nonpathogenic homology groups. Such microorganisms may include any of the following:

a) *Pseudomonas putida*—A gram negative rod that was isolated from fuel oil contaminated soil. This aerobic *Pseudomonas* falls within the non-pathogenic *P. flourescens* homology group;

b) *Acinetobacter johnsonii*/genospecies 7—A non-spore forming gram negative rod that was isolated from an Atlantic Ocean estuary off the coast of Hampton, N.H. These bacteria were selected for their ability to degrade crude oil and other petroleum hydrocarbons in marine environments;

c) *Alcaligenes faecallis* Type II—A gram negative rod that was isolated from fuel oil contaminated soil. *Alcaligenes faecallis* Type II. These bacteria are not gram positive and, thus, they are not *Staphylococci* sp., *Bacillus* sp., or *Streptococci* sp. Biolog analyses also excluded *Salmonella*, fecal coliform and *Shigella;* d) *Pseudomonas*-unidentified fluorescent—A gram negative rod that was isolated from fuel oil contaminated soil. This aerobic *Pseudomonas* falls within the non-pathogenic *P. flourescens* homology group.

A person of skill would further appreciate that the blends with biospheres can be used in in-situ methods where precision delivery is needed.

Further advantages of the blends with biospheres include the unique ability to engineer the dynamic viscosities of its gelatinous matrix, to slow down migration through the soil and stabilize the coverage of the matrix for prolonged periods across treated surfaces. This provides significant additional control that maximizes the opportunity for the bacteria to attach themselves to the target organic waste to be degraded or absorbed. Therefore, in complete contrast with conventional treatments, the present method minimizes wasting inoculant, while also helping to establish billions more bacteria far more quickly to make the process faster and much more predictable.

In further embodiments, fluorescence can be added to a biosphere so that the migratory patterns and stability of a gelatinous matrix can be tracked in the field and observed. In these embodiments, samples can be analyzed under UV light and/or by UV microscopy.

Further embodiments include kits which comprise a blend with biospheres. Such blends can be stored as a dry powder and mixed with water and a bacterial culture of choice prior to be used in the field.

The blend with biospheres and gelatinous matrix it creates has the potential to improve many commercial practices in the areas of water conservation, diffuse pollution management, land remediation, restoration of soils and the maintenance remediation of construction materials.

This invention will be further described by the way of the following non-limiting examples.

Example 1

A large field trial was conducted utilizing a conventional liquid bacterial culture in Phase 1 as shown in FIG. 1. See cells 1 and 4 before phase 2 treatment.

In Phase 2, both cells were treated with a blend comprising biospheres and a positive outcome was achieved. See FIG. 1, (Cells 2 & 3 not treated during Phase 1).

Moreover, the graph in FIG. 1 also delineates a second set of identical patterns of TPH biodegradation. These results are also significant, as they occurred in the treatment areas designated as the control locations during the study and, therefore, neither area had received any treatment whatsoever before Phase 2.

Ultimately, in these four heterogeneous cases, analysis had demonstrated identical patterns of biodegradation. Thus, the indicated change in TPH concentrations was due to biodegradation that resulted from the blend with biospheres in-situ remediation procedure carried out in the second phase of this environmental study. See FIG. 1. (Cells 2 & 3 not treated during Phase 1).

Additional studies were conducted and demonstrate the overall reduction in contaminant mass that was achieved after the in-situ remediation procedure with a blend comprising biospheres that was completed in the second phase of the same environmental study. These results are reported in FIG. 2 alongside instructive comparative data taken from the conventional in-situ bioremediation treatments that were performed in Phase 1 of the study. These results also verify the only significant reduction in pollution that had occurred on the site, over a period of eight years of scientific monitoring, was due to the biodegradation that resulted from utilizing the blend with biospheres.

Another distinction between conventional liquid culture and a blend with biospheres can be observed in shelf-life studies where random examples are taken at a specific point of final production and stored in separate twenty liter containers so that periodic samples can be taken for analysis to assess microbial viability over various periods of time. As shown in FIG. 3, various microbial cultures remained viable after 28 weeks in storage.

Overall, after fourteen weeks, these laboratory results demonstrated three blends with biospheres had sustained strong viability, one blend had sustained moderate viability and the liquid culture, used as the control, had sustained only a low level of viability. See FIG. 3.

After 28 weeks, the results demonstrated all four blends had sustained strong viability juxtaposed with the liquid culture that demonstrated no activity. See FIG. 3.

The results from this study are particularly instructive because various blends with biospheres tested and the control were all produced from the same batch of liquid culture.

While particular embodiments of the present biomolecular zonal compositions and methods have been described herein, it will be appreciated by those skilled in the art that changes and modifications may be made thereto without departing from the invention in its broader aspects and as set forth in the following claims.

The invention claimed is:

1. A composition comprising a blend of rechargeable biospheres and water, and optionally bacteria, biological and/or chemical reagents, wherein the biospheres are cellulosic biopolymers and have a free swell absorption capacity, wherein the composition is formable into an environmentally responsive gelatinous matrix which delivers and sustains bacteria, biological and/or chemical reagents in situ.

2. The composition of claim 1, wherein the biospheres gradually release moisture.

3. The composition of claim 1, wherein the viscosity of the composition is from 6 centipoise (cps) to 217 centipoise (cps).

4. The composition of claim 1, wherein the viscosity of the composition is from 217 centipoise (cps) to 1,159 centipoise (cps).

5. The composition of claim 1, wherein the viscosity of the composition is from 1,236 centipoise (cps) to 5,021 centipoise (cps).

6. The composition of claim 1, wherein the viscosity of the composition is from 5,021 centipoise (cps) to 47,311 centipoise (cps).

7. The composition of claim 1, wherein the biospheres are sized in the range from 500 nanometers to 80 microns.

8. The composition of claim 1, wherein the biospheres have a maximum free swell absorption capacity of 1200 times by weight.

9. The composition of claim 1, wherein the biospheres have a minimum free swell absorption capacity of 400 times by weight.

10. A method for bioremediation in situ, the method comprising:

preparing a blend of liquid bacterial culture with biospheres, wherein the biospheres are cellulosic biopolymers and sized in the range from 500 nanometers to 80 microns and have a minimum free swell absorption capacity of 400 times by weight and a maximum free swell absorption capacity of 1200 times by weight;

applying the blend at a site in need of bioremediation; and forming a gelatinous matrix with the blend.

11. A method for delivering and/or hosting biological and/or chemical reagents in a gelatinous matrix, the method comprising:

obtaining biospheres which are cellulosic biopolymers and sized in the range from 500 nanometers to 80 microns and have a minimum free swell absorption capacity of 400 times by weight and a maximum free swell absorption capacity of 1200 times by weight;

mixing the biospheres with a bacterial and/or chemical reagent to form a mixture; and forming a gelatinous matrix with the mixture.

* * * * *